(12) United States Patent
Pulido et al.

(10) Patent No.: US 9,301,672 B2
(45) Date of Patent: *Apr. 5, 2016

(54) DENTAL SCANNER DEVICE AND SYSTEM AND METHODS OF USE

(71) Applicant: Apollo Oral Scanner, LLC, Miami, FL (US)

(72) Inventors: Alfonso Fernandez Pulido, Madrid (ES); David De Pablos Garcia, Madrid (ES)

(73) Assignee: APOLLO ORAL SCANNER, LLC, Miami, FL (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/666,229

(22) Filed: Mar. 23, 2015

(65) Prior Publication Data

US 2015/0238287 A1 Aug. 27, 2015

Related U.S. Application Data

(63) Continuation-in-part of application No. 14/286,650, filed on May 23, 2014, now Pat. No. 8,989,567, which is a continuation-in-part of application No. PCT/ES2012/070834, filed on Nov. 28, 2012.

(51) Int. Cl.
| | |
|---|---|
| *A61C 9/00* | (2006.01) |
| *A61C 13/00* | (2006.01) |
| *G01B 11/24* | (2006.01) |
| *A61B 1/00* | (2006.01) |
| *A61B 1/05* | (2006.01) |
| *A61C 1/08* | (2006.01) |
| *A61C 5/14* | (2006.01) |
| *A61B 1/24* | (2006.01) |
| *A61B 1/247* | (2006.01) |

(52) U.S. Cl.
CPC ......... *A61B 1/00172* (2013.01); *A61B 1/00147* (2013.01); *A61B 1/05* (2013.01); *A61B 1/24* (2013.01); *A61B 1/247* (2013.01); *A61C 1/088* (2013.01); *A61C 5/14* (2013.01); *A61C 9/0053* (2013.01); *A61C 13/0004* (2013.01); *A61C 13/0019* (2013.01); *G01B 11/24* (2013.01); *Y10T 29/49567* (2015.01)

(58) Field of Classification Search
CPC .. A61C 9/0053; A61C 51/14; A61C 13/0004; A61C 13/0019; A61C 1/088; A61B 1/05; A61B 1/00147; G01B 11/24
See application file for complete search history.

(56) References Cited

U.S. PATENT DOCUMENTS

| | | | | |
|---|---|---|---|---|
| 3,382,781 | A * | 5/1968 | Hamilton | 396/16 |
| 4,575,805 | A * | 3/1986 | Moermann et al. | 700/163 |
| 6,821,116 | B2 * | 11/2004 | Severance | 433/29 |
| 8,989,567 | B1 * | 3/2015 | Pulido et al. | 396/16 |
| 2003/0148243 | A1 * | 8/2003 | Kerschbaumer et al. | 433/29 |

(Continued)

OTHER PUBLICATIONS

International Preliminary Report on Patentability for PCT Application No. PCT/ES2012/070834, issued Jun. 5, 2015.
English Translation of International Search Report for PCT Application No. PCT/ES2012/070834.

(Continued)

*Primary Examiner* — W B Perkey
(74) *Attorney, Agent, or Firm* — Ted Whitlock

(57) ABSTRACT

A three-dimensional (3D) scanner device for generating a three dimensional (3D) surface model of shaped objects, such as dental structures, applicable for use in the field of dentistry, particularly to dental prosthetics manufacturing. Methods and systems relating to the device are also disclosed.

20 Claims, 5 Drawing Sheets

(56) References Cited

U.S. PATENT DOCUMENTS

2005/0019732 A1* 1/2005 Kaufmann et al. ............ 433/213
2006/0154198 A1* 7/2006 Durbin et al. .................. 433/29
2008/0027279 A1* 1/2008 Abou El Kheir ............. 600/111
2013/0209954 A1* 8/2013 Prakash et al. ................. 433/29

OTHER PUBLICATIONS

English Translation of Written Opinion for PCT Application No. PCT/ES2012/070834.

Logozzo, S., et al., A Comparative Analysis of Intraoral 3d Digital Scanners for Restorative Dentistry, The International Journal of Medical Technology, vol. 5, No. 1 (2011).

* cited by examiner

DENTAL SCANNER DEVICE AND SYSTEM AND METHODS OF USE

BACKGROUND OF THE INVENTION

The subject invention relates to a scanner device for generating a three dimensional (3D) surface model of arbitrarily shaped objects, such as dental structures, preferably applicable for use in the field of stomatology, dentistry, or orthodontics, and particularly to dental prosthetics manufacturing. More specifically, the subject invention includes an intraoral 3D dental scanning device and methods for imaging and visualizing teeth or gingivae surfaces, including the conformation thereof.

Three-dimensional (3D) diagnostic and therapeutic modeling of teeth and gingivae have been traditionally obtained by mainstream techniques, such as using replicas obtained from alginate-impressed molds. Such replicas provide gingiva and tooth negative-image molds, which can later be converted into positive models, which may be scanned. However, these mainstream techniques pose problems and disadvantages which are manifold. These problems include: patient discomfort during the process of creating the mold, creation of imperfections and inaccuracies in the resulting mold, and the process can be slow and costly.

More recently, several state-of-the-art devices have been developed, e.g., panoramic dental X-rays, computerized dental tomographies, and optical scanning devices, that attempt to solve the problems posed by mainstream techniques. Optical scanners are devices which can capture and record information from the surface of an object, and generate that information into an image.

The use of scanners to determine the surface contour of objects by non-contact optical methods has become increasingly important in many applications including the in vivo scanning of dental structures to create a 3D model. Typically, the 3D surface contour is formed from a cloud of points where the relative position of each point in the cloud represents an estimated position of the scanned object's surface at the given point.

Such optical scanning devices have been developed and made commercially available for the dental market, and have been described in the patent literature incorporating a variety of technologies and configurations. For example, certain European patents have been identified as describing scanning devices, such as: EP 0825837, entitled, "Modular intra-oral imaging system video camera," provides a hand-held video camera to capture images of the inner part of the mouth and an optically aligned sensor which converts the captured images into usable data; ES 2383220, entitled "Intraoral dental imaging sensor and X-ray system, using such sensor," describes an intraoral dental radiological system equipped with a mouth-insertable X-ray imaging sensor having an image-detection matrix to provide electronic signals, and a light source to receive the matrix-generated signals; and ES 2324658 (T3), entitled "Laser-digitalizing system for dental applications" describes a laser digitizer that has a light source with collimation optics to generate a collimated light beam, a scanner optically coupled with the light source.

Optical scanning devices have also been patented or published in the United States, for example, in U.S. Pat. No. 6,648,640, entitled "INTERACTIVE ORTHODONTIC CARE SYSTEM BASED ON INTRA-ORAL SCANNING OF TEETH"; U.S. Pat. No. 4,837,732, entitled "Method and Apparatus for the Three-Dimensional Registration and Display of Prepared Teeth"; U.S. Pat. No. 4,575,805, entitled "Method And Apparatus For The Fabrication Of Custom-Shaped Implants"; U.S. Pat. No. 5,372,502, entitled "Optical Probe and Method for the Three-Dimensional Surveying of Teeth"; U.S. Pat. No. 5,027,281, entitled "Method and Apparatus for Scanning and Recording of Coordinates Describing Three Dimensional Objects of Complex and Unique Geometry"; U.S. Pat. No. 5,431,562, entitled "Method and Apparatus for Designing and Forming a Custom Orthodontic Appliance and for the Straightening of Teeth therewith"; U.S. Pat. No. 6,592,371, entitled "Method and System for Imaging and Modeling a Three Dimensional Structure"; and U.S. Pat. No. 7,004,754, entitled "Automatic Crown and Gingiva Detection from Three-Dimensional Virtual Model of Teeth"; as well as U.S. Publication No. 2006/0154198, entitled "3D Dental Scanner."

These systems and devices previously described all have various disadvantages in their design and use in practice. Commercially available 3D scanner systems have been developed for the dental market typically employ a handheld (by the operator), wand-type scanner in communication with a central (and typically large and bulky) computer/power source. In these systems, the operator moves the scanner over the area to be scanned and collects a series of image frames. The intraoral cavity represents a significant challenge for accurate in vivo 3D imaging of the surface of teeth and tissue. The ability to accurately measure the center of a scanning line is affected by the translucency of teeth, the variety of other reflecting surfaces (amalgam fillings, metal crowns, gum tissue, etc.) and the obscuration due to adjacent surfaces. Further, linear or rotational motion adds to error accumulation and the variation in size and curvature of human jaws makes a "one size fits all" scanner problematic.

In addition to the inaccuracies that can be introduced, these state-of-the-art devices and systems can be inconvenient to use, and inconvenient for the patient. In some cases, a technician must manually operate the handheld wand using a toothbrush-like motion and the results can depend on the dexterity and skill of the operator. Systems based on photographs taken by the various devices where software interprets and interpolates the photographic information into a final 3D image, can be time-consuming.

Thus, what is needed in the art is a 3D scanning device, and system, which can address and overcome disadvantages and limitations of the devices and systems which have been previously described and marketed.

The subject invention addresses and overcomes certain disadvantages of prior systems and devices by providing a completely integrated, unitary device, which is portable, and can be easily held by the patient during use. Thus, the invention provides a dental scanning device without certain flaws and inconveniences of the previously known state-of-the-art systems, capturing accurate 3D images using a fixed-reference system. No handheld wand is required, and no manual operation of the scanning probe is necessary by a technician or a patient, as the device and system is fully automated.

SUMMARY OF THE INVENTION

The subject invention comprises a 3D scanning device and system especially useful in the field of stomatology, dentistry, or orthodontics, and particularly to dental prosthetics manufacturing. The device and system of the invention is particularly applicable for imaging the surface characteristics of an object, including arbitrarily shaped objects, such as dental structures (e.g., teeth, gingiva, and the like), for generating a three-dimensional (3D) image and surface model of the object or objects. More specifically, the subject invention includes an intraoral 3D dental scanning device and method for imaging and visualizing teeth or gingivae surfaces, including the conformation thereof, useful for generating dental models and the manufacture of dental prosthetics therefrom.

Thus, the subject invention comprises a unitary, portable scanning device for performing a a three-dimensional scan of an object, wherein the device comprises a scanning probe comprising an extending arm coupled at one end to a mobility mechanism and at another end having a scanning probe head comprising an imaging source for generating an image of an arbitrarily shaped structure. The imaging source can employ optical, X-ray, radioisotope, magnetic, sound, CCD, or CMOS imaging. Optical imaging can include or employ visible, infrared, or ultraviolet light.

The mobility mechanism provides for extension/retraction, and lateral, movement of the scanning probe from a fixed reference point. The mobility mechanism and at least a part of the extending arm of the scanning probe is encased within a housing body formed as a hollow shell having a chamber for encasing at least a portion of a scanning probe and encasing the mobility mechanism which moves the scanning probe.

The housing body preferably comprises an opening through which the scanning probe extends for scanning the object.

The device of the invention can be configured as a table-top scanning device. More preferably, the device is configured as a portable, or hand-held intraoral scanner for scanning dental structures in the mouth of a patient or subject.

For use as an intraoral scanner, the housing body opening is configured to receive or engage a mouthpiece. The mouthpiece has a top and bottom face separated by side walls to form a hollow bite fixture onto which the subject can bite down upon during a scanning procedure. The bite fixture has distal and proximal ends, wherein the proximal end engages with the opening of the housing body and is open for communicating with the chamber of the housing body. The open proximal end of said mouthpiece receives and allows movement of the scanning probe therewithin during a scanning procedure.

Preferably, at least one of the top or bottom faces of the bite fixture comprises a transparent or translucent window to allow communication between the optical imaging source and imaging receiver or sensor.

The scanning device of the invention can comprises a chassis holding a mobility mechanism for moving the extension arm and scanning probe. The scanning probe comprises a scanning probe head holding at least one imaging source or a plurality of imaging sources. Preferably, the mobility mechanism moves the scanning probe automatically in a pre-programmed scanning pattern without further manipulation by an operator. Thus, the scanner device of the subject invention, which employs automatic movement and a pre-programmed scanning pattern of the extension arm and scanner probe, provides for a wand-less scanning probe and scanning procedure.

Advantageously, the pre-programmed scanning pattern provides movement only along an X-axis and Y-axis, or along a horizontal plane, and does not provide or allow movement of the extension arm or scanner probe head in a non-vertical (Z-axis) direction.

The subject invention further concerns a method of performing a dental scan, said method comprising the steps of: (1) providing a scanning device as described herein, and (2) performing a scanning procedure on a subject or patient.

A method of the subject invention can further comprise the step of: printing, milling, or 3D-printing a dental structure using the information obtained from the scanning procedure.

In addition, the subject invention relates to a system for carrying out a dental scan on a patient, wherein the system comprise a portable scanning device as described herein, and an external device selected form a printer, a milling machine, and a 3D printer. The scanning device can include an integral mouthpiece or bite fixture or can optionally include a separate mouthpiece or bite fixture which matingly engages the housing of the device. a separate mouthpiece, an optional cable for connecting the device to an external printing, milling or 3D printing device, and a carrying case for containing said device, mouthpiece and optional cable.

The system of the invention can further include a connecting cable for connecting said device to an external printing, milling, or 3D printing device and may optionally include a carrying case for one or more components of the device, such as the housing, bite fixture, connecting cables or external printer or milling device.

BRIEF DESCRIPTION OF THE DRAWINGS

FIGS. 3A-3C show various views of the mouthpiece wherein:

FIG. 3A is a perspective view of an embodiment of a mouthpiece for the subject device, illustrating the transparent or substantially translucent top or bottom panel thereof, and a circumferential flange positioning stop;

FIG. 3B is a perspective view of an embodiment of a mouthpiece for the subject device, showing an exploded view of the transparent or substantially translucent top or bottom face of the mouthpiece;

FIG. 3C is a perspective view of an embodiment of a mouthpiece for the subject device, illustrating the scanning probe within the chamber formed by the mouthpiece.

DETAILED DESCRIPTION OF THE INVENTION

Figure 1:
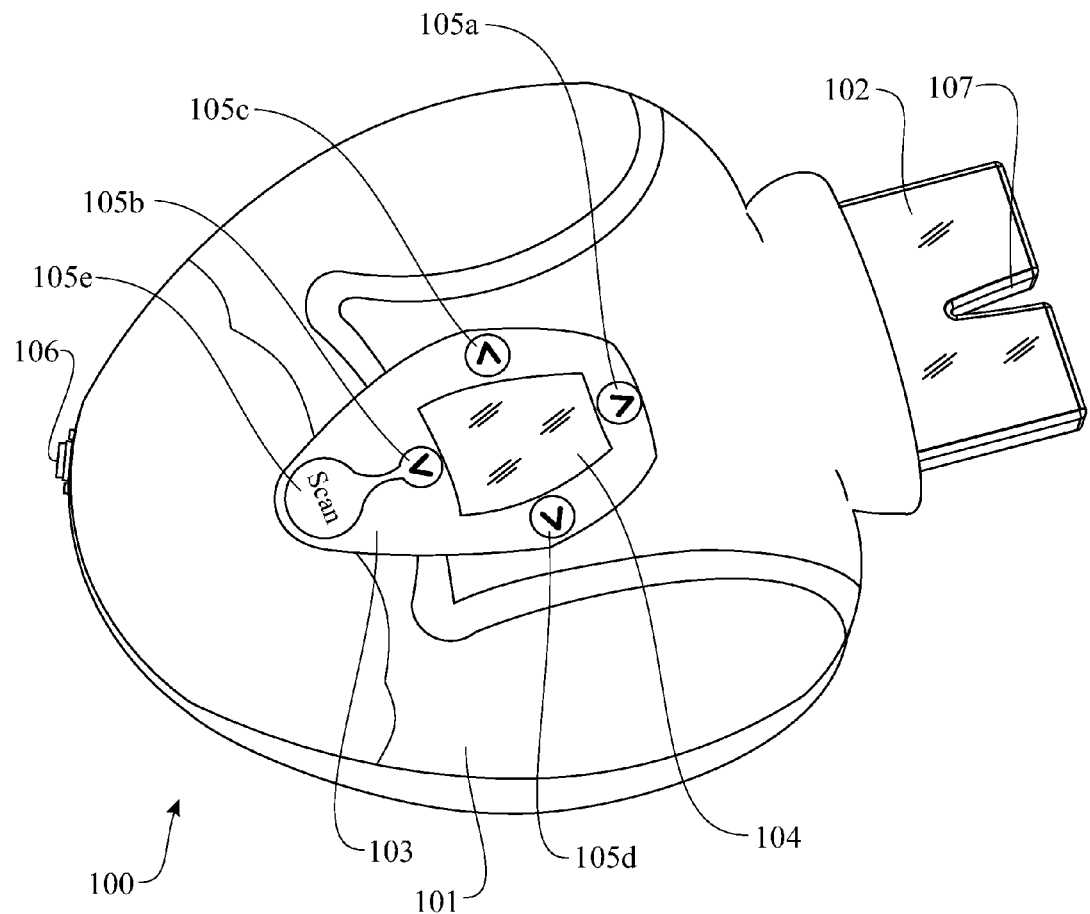
FIG. 1 shows an embodiment of a device according to the subject invention, illustrating a top or bottom view of the housing body and mouthpiece in an engaged configuration.

A device of the subject invention comprises, in a preferred embodiment, a housing body that is preferably capable of being held in the hand or hands of a person. By the phrase, "capable of being held in the hand or hands of a person," is meant that the housing body is configured having a size and weight that can be readily held in one or both hands by a user or scanning subject during a scanning procedure.

The housing body of the device contains or encases a chassis providing a mobility mechanism for moving, guiding, or directing a scanning probe coupled to the mobility mechanism. By providing a mobility mechanism for operating the movement of the scanning probe in a fixed or pre-programmed pattern relative to the scanning subject, the device and its use can advantageously provide a fixed reference point for the scanning probe, obviating the need for a hand-manipulated wand.

The scanning probe comprises an arm or stem coupled to the mobility mechanism at a first proximal end of the arm, and having a scanning head positioned at an opposite, distal end of the arm. The scanning head comprises an imaging source affixed thereto or integral therewith, such as an infrared or light-emitting diode (LED) or laser light source, and can comprise a sensor, transducer or receiver for capturing an image generated by the imaging source when projected onto the surface of the object, such as dental structures. The scanning head can further include a camera or a plurality of cameras for photographic or video images which can be converted to three-dimensional images using available computer software or other computer technology.

Thus the scanning head can comprise one or more imaging components, such as but not limited to an optical imaging source, for generating an imaging source and capturing or storing the generated image, as described and well understood in the art. It would be readily understood that the imaging source can alternatively employ imaging generated by one or more of optical, X-ray, radioisotope, magnetic, sound, charge coupled device (CCD), or complementary metal oxide semiconductor (CMOS) imaging sources as are currently used in the art, or other imaging sources in development. Optical imaging includes, and is not limited to, visible, infrared, or ultraviolet light. Advantageously, the optical imaging source does not require a collimator for focusing the imaging light source and can be provided with or without a collimator. Accordingly, a device of the subject invention can comprise a collimator or can be collimator-free.

The housing body of the device, which is preferably formed as a molded plastic shell, is provided to enclose or completely encase both the mobility mechanism and at least a portion of the scanning probe (such as the probe arm) when the device is "at rest," i.e., when in an "off" position or not in scanning mode. The housing body comprises an opening whereby, during its operation, the scanning head of the scanning probe, and typically a portion of the arm of the scanning probe, extends outside the housing body to carry out an imaging process or scan, when "on" or in scanning mode.

The scanning probe can be partially or completely contained within the housing body when a scan is not being performed, and can be moved outward by the mobility mechanism to project outside the housing body for intraoral scanning of dental structures (e.g., teeth, gingiva, and the like) in a patient.

In a typical embodiment of the invention, one end of the probe arm is coupled to the mobility mechanism within the housing body, wherein said probe arm extends outside the housing body, and the probe head is also outside the housing body.

Thus it would be understood that one embodiment of the scanner device of the invention is useful as a table-top scanner of an object.

In one preferred embodiment for use as an intraoral scanner, the probe head can be protected outside the housing body by a mouthpiece which chambers or encloses the probe head during the scanning operation. It is contemplated that the entire scanning probe can be withdrawn inside the housing body for full protection of the scanning probe, including the probe head, when in an "off" position or not performing a scanning procedure.

The optional mouthpiece, as further described herein below, used for intraoral scanning can be formed as part of or integral with the housing of the scanning device, or can be a separate component of the device. Preferably, a mouthpiece forming a separate component of the scanning device can matingly engage and be received by the opening in the housing. More preferably, the mouthpiece is formed as a bite fixture which is held in the subject's or patient's mouth during the scanning procedure and can be disengaged from the scanning device and replaced for each user.

Advantageously, the subject device can be portable, and completely self-contained and hand-held during a scanning operation, meaning that the device does not require a separate hand-held probe wand cabled to an image processor. Hand-held probe wands, and operation thereof by hand, are well known in the industry, but can introduce extraneous linear and rotational motion during hand operation of the wand, which can result in image artefact and increased time for image processing. These disadvantages of a separate, hand-held probe wand can be due to, for example, a requirement for the image processor to continuously or frequently re-calculate reference positioning, which can increase total time of the scanning procedure.

By contrast, the subject device does not include or require a hand-held wand, i.e., the device is wand-less or wand-free, whereby the scanning probe has a fixed reference position at all stages of the scanning procedure. The scanning probe of the subject invention does not require manipulation by an operator at any time. The movement of the scanning probe of the subject device can preferably be driven by a mobility mechanism operated by a motor, such as an electric or electronic stepping motor. When engaged or turned "on", the motor-driven mobility mechanism moves the scanning probe automatically in a pre-programmed scanning pattern without further manipulation by an operator.

In accordance with the subject invention, the device is unitary, whereby the entire imaging unit, including the scanning probe, is controlled and operated by the device, itself, while the mouthpiece is held in a fixed position in the mouth of the subject, thereby providing a fixed reference position for the scanning probe. Thus, the scanning probe, itself, is not hand-held or otherwise manipulated by hand; rather the entire unit is held in a steady or fixed position during the scanning procedure, and the scanning probe, which is integral with the unitary device, is directed by the mobility mechanism to move in a controlled or pre-programmed pattern to carry out a scan. Such pre-programmed pattern is typically an arc pattern, corresponding to the dental arch of a patient or subject on which the scan is performed.

The housing body, in a preferred embodiment, is ergonomically designed having a size and shape, such as rounded or contoured edges, for being easily held by a patient during use. The housing body is preferably formed by plastic or other light material, molded or otherwise shaped to form a shell structure having a hollow chamber therein. The chamber formed within the housing body shell, which contains the mobility mechanism coupled to, and for movement of, the scanning probe, further encases the electronics and mechanical positioning apparatus for controlling the movement and operation of the scanning probe. For example, the mobility mechanism for moving the scanning probe comprises a chassis, onto which the positioning apparatus is provided, including the operational control mechanism for movement of the probe.

The positioning apparatus can include an extension arm coupled to the stem or arm of the scanning probe, to extend and retract the scanning probe to and from within the chamber of the housing body. For ease of reference, the movement of the scanning probe is said to move outward, in a distal direction from the center of the housing body, and inward, in a medial or proximal direction toward the center of the housing body. The chassis can further have coupled thereto a lateral rod or gear system providing for lateral (horizontal or side-to-side) movement of the scanning probe.

These mechanisms and apparatus for movement and positioning of the scanning probe, i.e., for extending/retracting and for lateral movement of the scanning probe are well understood within the mechanical arts. Preferably, the scanning probe is moved only in the in/out and side-to-side directions, and does not move vertically, retaining a constant horizontal plane, within the confines of the mouthpiece, during operation.

The mechanical positioning mechanism can be controlled by electronics, such as an electronically driven motor, which can direct and control the movement and position of the scanning probe. A preferred embodiment of the device is powered by a motor driven by electricity or by battery-stored electricity, wherein a battery or other power source can also be contained within the housing body. Alternatively, the electric motor can be connected to an external electrical power source by a cable or electrical cord.

The electronics directing the movement of the scanning probe can be controlled by computer software, provided and stored within or without the housing body, and the software can provide a menu of functions, such as ON/OFF, SCAN, or other desired functions, operated by one or more switches or buttons positioned on the outer top or bottom face of the housing body. Preferably, the device comprises a set of switches or buttons on each of the top and bottom face of the device housing.

Providing two sets of switches or buttons, one on each of the top and bottom face of the housing body, allows for the device to be operated in dual positions, i.e., upward-facing position and downward-facing position. By "upward-facing" is meant that the probe head and light source are positioned to face upward, toward the top teeth during a dental scan; by "bottom-facing" is meant that the probe head and light source are positioned to face downward, toward the bottom teeth during a dental scan. Therefore, for conducting a complete scan of the top and bottom teeth of a patient, the device can advantageously be positioned in a first direction, e.g., upwardly, to scan the upper teeth, then turned approximately 180° and positioned in the other direction, e.g., downwardly, to scan the bottom teeth. A housing body having switches or buttons on both the top and bottom face can facilitate operation of the device in either upward or downward facing position.

The housing body can further comprise a connector or port for engaging a cable for communication with a computer or image processor for processing or storing information received from the sensor, transducer or receiver of the scanning probe. Alternatively, the device can comprise a wireless transmitter/receiver for wirelessly communicating with a computer, whereby the wireless transmitter/receiver can be provided integral with the device or housed within the housing body.

Positioning of the device and scanning probe for optimal intraoral scanning results is facilitated by the mouthpiece or "bite fixture", which engages the device and provides a protective cover for the scanning probe. Configured for being easily and comfortably held in the patient's mouth during a scanning procedure, the mouthpiece is preferably a generally flat rectangular housing having side walls and top and bottom walls forming and surrounding a generally flat, rectangular hollow chamber.

The top and bottom walls provide a surface for the patient to bite down onto during the scanning procedure, advantageously providing a fixed position of the teeth during a scanning procedure. This fixed position of the teeth on the mouthpiece provides for and facilitates a fixed reference point relative to the scanning probe, which moves in a pre-programmed pattern during a scanning procedure. Thus, by virtue of the fixed intraoral position of the bite fixture, the scanning probe retains a stable relative position in the mouth of the patient or subject and retains a fixed scanning pattern relative to, and irrespective of, any movement or positioning of the head of the subject or patient.

This fixed intraoral positioning of the device provides an advantageously comfortable experience for the patient because the scan to be conducted without strict restraint or immobilization of the patient's or subject's head using an external head-restraining device. The fixed intraoral position of the bite fixture can provide for diminished risk of scanning artefact caused by inadvertent head movement of the patient or subject during the scanning procedure, and allows the scanning procedure to be carried out successfully even in the event of slight head movement on the part of the patient or subject.

The mouthpiece of the device can be configured to engage, and preferably be separable from, the opening provided in the housing body. The mouthpiece is provided as a platform having at least top and bottom faces spaced apart from one another, onto which the patient or scanning subject can bite down onto during a scanning procedure. The top and bottom face are preferably substantially solid planar panels, connected to, but spaced apart from, one another by substantially planar side walls which, together, form or bound the substantially rectangular hollow chamber.

The mouthpiece advantageously serves to facilitate positioning and stabilization of the "bite" by the patient or scanning subject, so that the teeth or dental arch being scanned are held in a fixed position during the scanning procedure. The mouthpiece can further serve to protect the scanning probe as it extends into the oral cavity during operation of the device during a scanning procedure.

At least one top or bottom face of the mouthpiece comprises a transparent, or sufficiently translucent window, to allow the scanning light source to penetrate therethrough, and to allow return of light information to the sensor, transducer, camera, or receiver on the scanning probe head to perform a scanning procedure. Generally, the transparent or translucent window is a panel sized to correspond or conform to the entire dental arch being scanned. Different shapes and configurations of the transparent or translucent window are contemplated and are not critical to the invention so long as the configuration provides for scanning the targeted teeth of the patient or subject.

As stated, the front end of the mouthpiece, facing toward the patient and within the oral cavity during operation or use, can be closed or open, but is preferably closed by a front wall. The opposite end of the front end or wall is open to communicate with the hollow chamber of the housing body. The hollow chamber formed within the mouthpiece receives the scanning probe and provides an area for the scanning probe to enter, extend, retract, and move laterally and perform a scan.

Various shapes and configurations can be used for the mouthpiece so long as it provides for positioning in the mouth, a bite platform, and allows for movement of the scanning probe therein. A preferred embodiment can comprise a shape conforming generally to the shape of the dental arch. Positioning guides, such as printed, formed or grooved indicia, or contours can be provided on the mouthpiece, but a generally flat wall comprising the scanning widow is preferred in order to reduce optical artefact during the scanning procedure.

In a preferred embodiment, however, the generally rectangular mouthpiece can include a generally "V"-shaped or "U"-shaped open area which provides room for the patient's tongue to move more freely, facilitating breathing and reducing the likelihood of inducing a feeling of choking or a "gag-response" by the patient.

As mentioned, it is preferred that the mouthpiece is separable from the housing body, and more preferably, easily engaged to or disengaged from, i.e., easily separable from and affixable to the housing. To facilitate ease of engagement or disengagement from the housing, the opening of the housing for receiving the mouthpiece or bite fixture can be matingly configured to the engagement end of the mouthpiece or bite fixture.

A separable mouthpiece can facilitate its use under sanitary conditions, either allowing removal of the mouthpiece from the housing body to perform cleaning/sterilization procedures between uses or, when made from cost-effective material, such as an inexpensive plastic, can be provided as a disposable, one-time-use-only mouthpiece that can be affixed to the scanning device for each use, and discarded thereafter.

It would be understood that the mouthpiece can be formed as an integral part of or unitary with the housing body. While an integral mouthpiece formed as part of the device can include a removable cover or sleeve provided for each patient for maintaining sanitary conditions, this integral mouthpiece embodiment does not readily provide for different sizes of mouthpieces to accommodate different sizes of mouths, such as adult-sized and child-sized mouths. Accordingly, a preferred embodiment comprises a separate and removable mouthpiece, which is not formed permanently integral with the housing body.

A removable cover or sleeve can be provided for the separable mouthpiece as well, and can be useful for maintaining sanitary conditions or can provide cushioning or a comfortable mouth-feel for the patient or subject. It is preferred that a material used for the bite fixture cover or sleeve does not interfere with communication between the scanning source and sensor or receiver.

An embodiment of the invention comprising a separable or removable mouthpiece can provide the capability of at least two or more sizes of a mouthpiece. For example, one size of mouthpiece can be provided for adult mouths, and another, smaller size of mouthpiece can be provided for children. Intermediate or larger or smaller sizes can also be provided. Each size of mouthpiece has the same configuration, i.e., is the same size, at its end engaging the housing body, so that multiple sizes of mouthpieces can fit and engage with a single housing body of a device.

In one preferred embodiment, the mouthpiece comprises at least one flange or annular ridge around its circumference so that it provides a positional "stop" or indicator when properly engaging with the housing body. This flange or annular ridge can further serve as a positional indicator for proper placement of the mouth onto the mouthpiece during a scanning procedure.

The device, as described can be included as a system for scanning dental structures, wherein the system comprises the components of the device as described, and can further include external, in-line devices which are used in conjunction with the scanning device for providing a dental scan. External devices can receive, process, or utilize the information provided by the dental scan. For example, a system of the subject invention can comprise a printer for printing a photograph from the scan information, a milling machine for constructing a prosthetic dental structure (e.g., a crown or denture) from the scan, or a 3D printer for printing a prosthetic dental structure.

Methods of using a scanning device of the subject invention are also within the scope of the invention. For example, a method of use can include the steps of (a) providing a scanning device as described and (b) performing a scanning procedure on a subject or patient. The method can further comprise an additional step (c) of printing, milling, or 3D printing a dental structure using the information obtained from the scanning procedure.

Advantageously, the scanning device of the subject invention can provide a method for scanning teeth and gingivae without the need for imaging powder or imaging gel applied or administered to the teeth or gingivae of the patient or subject. Thus the subject method can be a powder-free or gel-free scanning procedure, which can save time, cost, and reduce discomfort to the patient or subject.

To describe and illustrate the components of a device of the invention, reference is made to the accompanying drawings, whereby: FIG. 1 shows an embodiment of a device 100 according to the subject invention, illustrating a top or bottom view of the housing body 101 and mouthpiece 102 in an engaged configuration. Reference is made to "either" the top face or bottom face of the device because, in a preferred embodiment, the device is symmetrical wherein the top and bottom faces are identical or at least substantially identical so that the device can be operated in an identical or substantially identical manner when facing upward or downward.

During operation, the device is positioned, for example, upwardly to perform a scan of an upper dental arch, and the device may then be rotated approximately 180° to face downward for scanning, for example, the lower dental arch. In both instances, a control panel 103 provided on each top and bottom face, provides for easy access and manipulation of the control panel on the "upper" face (facing upward at the time of operation).

Thus, as shown here, the outer (top or bottom) face comprises a control panel 103 integral with the face wherein the control panel comprises a menu screen 104 for viewing a menu of available operations or functions on menu screen 104. The operation of the device can be controlled by manipulating one or more buttons or set of buttons provided as part of the control panel. Here, an embodiment is shown having a set of five (5) buttons, specifically, buttons 105a, 105b, 105c, 105d, and 105e, for controlling the menu and function or operation of the device.

Buttons 105a and 105b, for example, can manipulate a scrolling function of a menu display, allowing the user to scroll up or down on a displayed menu page; buttons 105c and 105d, can control the selection of different pages of the menu, for example, button 105c providing the operation to return to a previous page of the menu, and button 105d providing an operation of moving forward to a next page of the offered menu. Button 105e can be used for initiating the "scan" operation, and can further perform "on/off" functions or the like.

It would be readily understood that a great variety of styles and designs can be incorporated into the control panel, and the particular style or design is not critical, so long as the device provides user-friendly options for functionality and operation of the device.

The housing body can be molded or otherwise fabricated using plastic or other appropriate lightweight material, and can be formed as a single unit, or can be formed as sections, example upper and lower halves, which are fitted together to form the single housing body unit.

Mouthpiece 102 is shown engaged with an opening (not shown) formed in one end of housing body 101. The embodiment of mouthpiece 102 as shown here, comprises a transparent panel forming a top or bottom face of the mouthpiece. In addition, mouthpiece 102 illustrates a substantially "V"- or "U"-shaped cut-out area 107 formed therein. This is a preferred configuration for a mouthpiece of the invention, conforming generally to the shape of the dental arch, and further advantageously minimizing obstruction of a patient's airway, and gag-response, while permitting the scanning probe to reach the full dental arch during a scanning procedure.

At an end of the housing body, opposite the mouthpiece, is a connector port 106, for coupling the device, via a cable, to a computer, image processor, milling machine, printer (e.g., a 3D printer), or the like for transferring information received by the scanning probe to an external device. This connector can alternatively provide for wireless connection, i.e., be configured as a wireless transmitter, for wirelessly transferring image information to an external device. It would be understood that the location of the connector can be at any position on or within the housing body, so long as it fits within the function and design of the device.

Alternatively, this connector port 107 can be configured as part of a male/female coupling means for coupling the device to a base or stand, providing for hands-free use of the device during a scanning procedure (see, for example, FIG. 5, and accompanying description, below).

Figure 2:
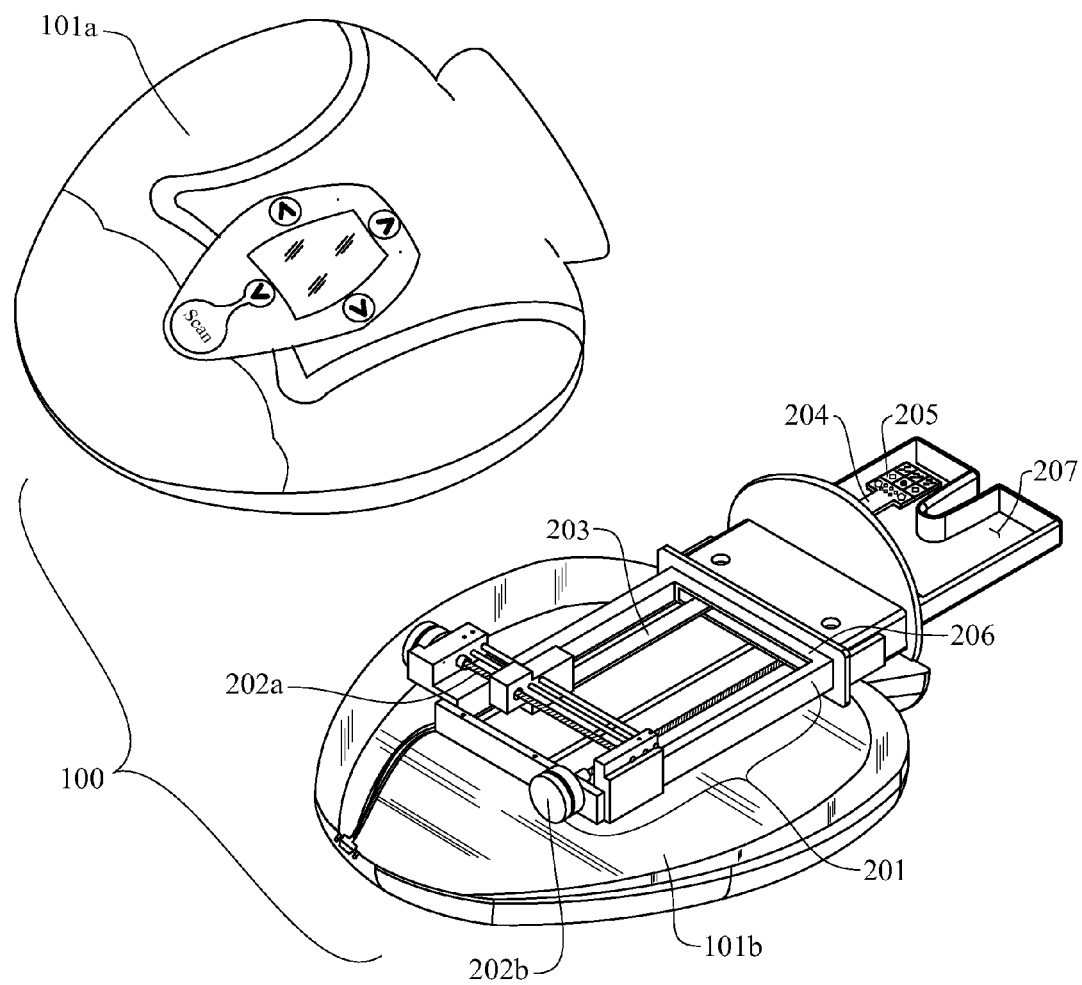
FIG. 2 is an exploded top or bottom perspective view of an embodiment according to the subject invention, illustrating the chassis and scanning probe components housed within the housing body.

FIG. 2 is an exploded top or bottom perspective view of an embodiment of scanning device 100 according to the subject invention, illustrating the housing body 101 formed from two halves 101a and 101b. This view further illustrates a chassis 201 provided for holding a mobility mechanism coupled to and providing movement for a scanning probe 203 comprising a an arm or stem 204 and a scanning head 205.

The mobility mechanism comprises one or more stabilizing bars or rods and a rotating screw mechanism for lateral movement of the scanning probe 202a and one or more stabilizing bars or rods and rotating screw mechanism 202b for distal/proximal (in/out) movement of the scanning probe.

Further shown in FIG. 2 is opening 206 formed or provided at one end of the housing body, such that the mouthpiece can engage the housing body, and the scanning probe can extend from within the housing body into the chamber 207 of the mouthpiece.

Figure 3A:
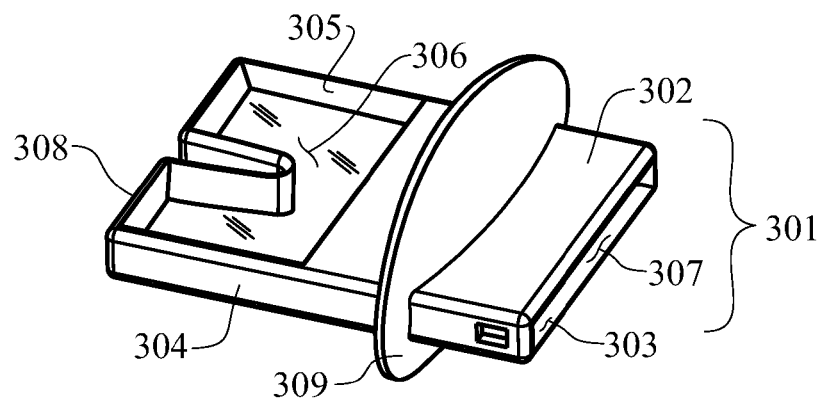
Figure 3B:
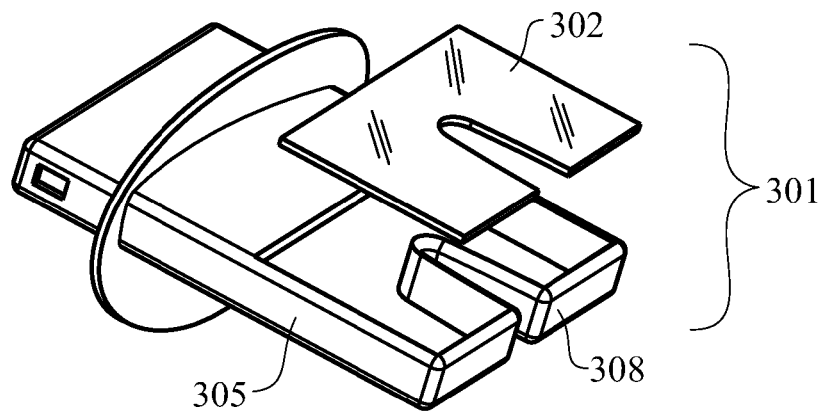
Figure 3C:
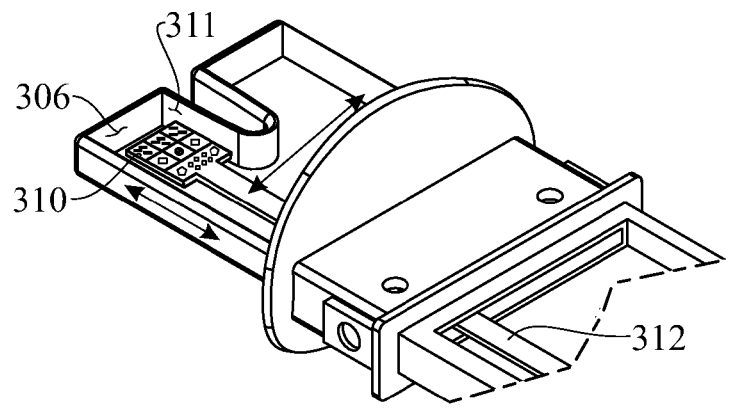

FIGS. 3A-3C show various views of one embodiment of the mouthpiece component of the device of the invention wherein: in FIG. 3A is illustrated mouthpiece 301 comprising a top face 302 and bottom face 303, spaced apart from one another by side walls 304 and 305 forming a hollow chamber 306 therein.

Open end 307 engages with the housing body of the device, and provides for communication with the chamber of the housing body and for receiving a scanning probe (not shown) in the formed chamber of the mouthpiece. An intraoral end of the mouthpiece can be open or closed, but is preferably closed by front (intraoral) wall 308.

In the embodiment shown, top face 305 comprises, at least in part, a clear or transparent plastic material for allowing a scanning source, such as infrared or laser light, to pass therethrough without interference or distortion of the light source, or the information returning to a sensor, receiver, or transducer provided in or on the scanning probe head.

Also illustrated in FIG. 3A is a circumferential (or annular, if substantially circular or ovoid shaped) flange or ridge 309 which can provide a positional "stop" for engaging the mouthpiece to the housing body. The flange or ridge 309 can also function as a "stop" for the lips or mouth of the subject.

In FIG. 3B, the mouthpiece 301 of FIG. 3A is shown in an exploded view, illustrating the clear or transparent top face 302 of mouthpiece 301, and showing front (intraoral) wall 308.

FIG. 3C provides illustration of scanning probe 310 comprising a scanning head 311 inside the mouthpiece chamber 306, coupled to an arm or stem portion 312 extending from within the housing body. The scanning probe 310 can move distally/proximally (in/out) and laterally in the directions depicted by the arrows. The scanning probe head can comprise one or more imaging sources, such as a light source for generating the image. In one preferred embodiment, the imaging source can comprise a plurality of light sources, e.g., LED laser light. The scanning probe head can preferably comprise at least one light source, more preferably about four to about ten light sources, and typically about six to about eight light sources. These plurality of light sources are well understood in the art to be configured to communicate together to generate a single 3-dimensional image.

Figure 4:
FIG. 4 illustrates an embodiment of the device of the invention, hand-held and in use by a scanning subject during a scanning procedure.
Figure 5:
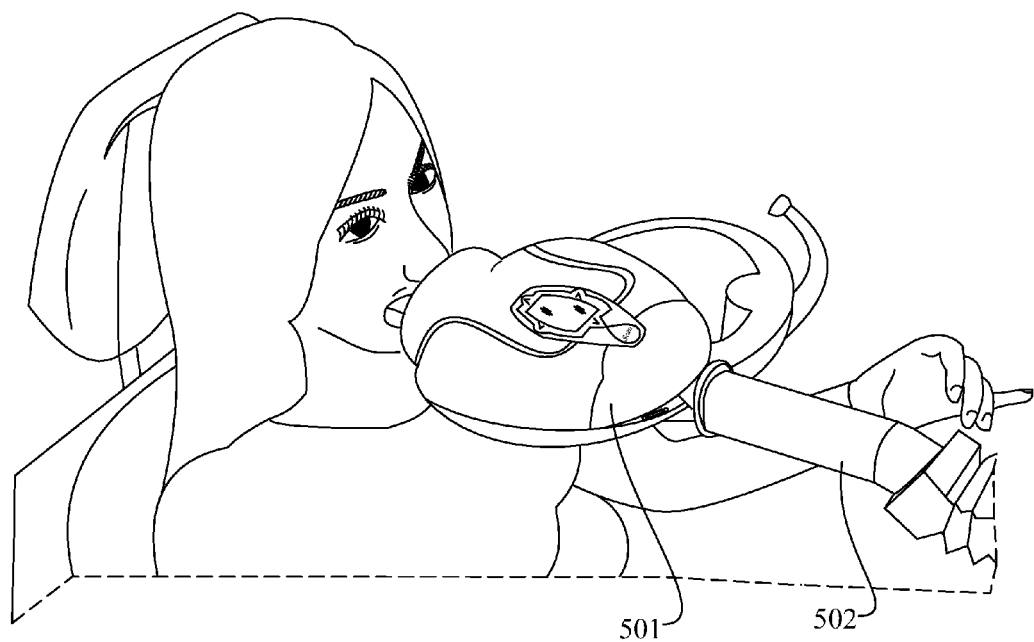
FIG. 5 illustrates another embodiment of a device of the invention, illustrating a mounted embodiment, which can be affixed to a base.

FIGS. 4 and 5 illustrate one embodiment of a device of the subject invention in use. Specifically, FIG. 4 shows a handheld embodiment, wherein device 401 is held by the subject 402 during operation of the device to conduct a dental scanning procedure. FIG. 5 illustrates an alternative embodiment, mentioned above, whereby the device 501 is coupled to or mounted on a mounting base or stand (not shown) having an extension arm 502 for holding the device in position during a dental scanning procedure.

Having illustrated and described preferred embodiments of a device of the invention, said device can be used for performing a dental scanning procedure on a subject. In use, the device and mouthpiece are engaged together to form a single unit. The control panel is set to the desired function by the operator of the device and the mouthpiece, engaged with the device, is introduced into the oral cavity of the subject, positioned so that the mouthpiece contacts or positionally conforms to the entire dental arch. The subject preferably bites onto the mouthpiece for securing the position of the dental arch in relation to the mouthpiece and reducing the unnecessary movement of the device in relation to the dental arch during the scanning procedure.

The operator of the device then presses the "scan" function on the control panel to begin the scanning procedure, whereby the scanning probe automatically moves outward and extends to begin the scanning process at the desired location (e.g., tooth 1, 16, 17 or 32). The scanning probe head moves to sweep in at least two directions: one following the long axis of the scanning probe and its extending arm, and the other being lateral (perpendicular to the long axis of the scanning probe and its extending arm).

For the intraoral scanning, the scanning probe can comprise one or more of a detection sensor, laser sensors or similar devices integral with the scanning probe, or alternatively and preferably can comprise a camera to capture tooth-by-tooth sweep images from the dental arch and gingivae. These images are automatically generated as exact reproductions of the 3D images, as a result of their fixed and constant reference point in relation to the device or system.

The scanning probe moves in an arc to scan the entire dental arch of either the top or bottom teeth. If a full scan of all teeth is desired, the device can be removed from the mouth of the subject following a scan of a first (upper or lower) dental arch, rotated approximately 180°, and the process repeated for the other dental arch.

In a preferred embodiment, the vertical movement of the scanning probe is restricted, i.e., the probe only moves laterally or horizontally (side-to-side) and distally/proximally (out and in), but not vertically (up and down) or rotationally in relation to the mouth or the patient. Thus, the vertical, planar position of the scanning probe is maintained, whereby the scanning probe moves only in a single plane, and does not rise or fall, move up or down, or rotate or tilt during a scanning procedure.

This maintenance of a planar vertical position for the scanning probe provides a further advantage for the device, whereby the fixed position of the mouth on the mouthpiece and fixed reference point for the scanning probe is not affected by, and does not introduce additional motion artefact to the information generated by the scanning probe head. Vertical movement, tilting or rotational motion of the scanning probe can be a disadvantage of devices employing a hand-held wand comprising the scanning probe or scanning probe head.

Advantageously, the subject device is wand-less, i.e., it does not comprise a hand-held wand for hand-manipulation of the scanning probe. Instead, the scanning probe is manipulated for movement along a pre-set or pre-programmed arced pattern corresponding to the dental arch, using the chassis-mounted movement apparatus and mobility mechanism within the housing body, facilitating scanning using a fixed position reference point. Thus, the imaging processor is not required to relocate its reference position if the reference point is changed, such as can occur by use of a hand-held wand as the scanning probe. The device of the subject invention is therefore termed a "wand-less" or "wand-free" scanning device.

The subject device can be provided as a system, including a housing body comprising movement mechanism and scanning probe, and one or more separable mouthpiece. In addition, the system can comprise one or more connecting cable, mounting base and mounting arm, and one or more external device for receiving, processing or expressing information generated during the scanning procedure. For example, the system can include with a scanning device, a computer, image processor, milling machine, 3D printer or the like.

These components can also be provided in a carrying case which preferably has within the case, areas designated for each component, for easily and advantageously storing, carrying, and organizing the portable device and components therefor.

A method for performing a dental scan one or more teeth of a subject comprises the steps of (a) providing a scanning device having a fixed reference point for the scanning probe, as described and (b) operating the scanning probe to perform a scanning procedure on a subject or patient. The method can further comprise an added step of (c) printing, milling, or 3D-printing a dental structure using the information obtained from the scanning procedure. Moreover, the method can be carried out without use of a scanning powder or scanning gel; therefore the subject method is advantageously a "powder-free" or "gel-free" scanning method.

The invention claimed is:

1. A unitary, portable scanning device for performing a three-dimensional scan of an object, said device comprising:
   a scanning probe comprising a probe arm coupled at one end to a mobility mechanism and at another end having a scanning probe head comprising an imaging source for generating an image of an arbitrarily shaped structure,
   said mobility mechanism and at least a part of the probe arm of said scanning probe being encased within a housing body formed as a hollow shell having a chamber for encasing at least a portion of a scanning probe and encasing a mobility mechanism for moving the scanning probe,
   said housing body having an opening through which the scanning probe extends for scanning the object, and is adapted to receive or engage a mouthpiece which allows movement of the scanning probe therewithin during a scanning procedure.

2. The device of claim 1 wherein said device is configured as a table-top scanning device.

3. The device of claim 1 wherein said device is configured as a hand-held intraoral scanner for scanning dental structures within the mouth of a patient or subject.

4. The device of claim 3, said mouthpiece having top and bottom faces separated by side walls to form a hollow bite fixture onto which the subject can bite down upon during a scanning procedure.

5. The device of claim 1 wherein the imaging source employs imaging selected from optical, X-ray, radioisotope, magnetic, sound, charge coupled device, and complementary metal oxide semiconductor.

6. The device of claim 5 wherein the imaging source employs optical imaging.

7. The device of claim 6 wherein the optical imaging is selected from visible, infrared, and ultraviolet light.

8. The device of claim 4, wherein at least one of the top and bottom faces of the bite fixture comprises a transparent or translucent window to allow communication between the optical imaging source and imaging receiver or sensor.

9. The scanning device of claim 1, wherein the device comprises a chassis holding the mobility mechanism for moving the scanning probe.

10. The scanning device of claim 1 wherein the scanning probe comprises the scanning probe head holding the imaging source.

11. The device of claim 3 wherein the scanning probe head comprises a plurality of imaging sources.

12. The device of claim 1 wherein said mobility mechanism moves the scanning probe automatically in a pre-programmed scanning pattern without further manipulation by an operator.

13. The device of claim 12 wherein the pre-programmed scanning pattern comprises movement only along an X-axis and Y-axis, or horizontal plane.

14. The device of claim 12 wherein the pre-programmed scanning pattern comprises non-vertical (Z-axis) movement of the scanning probe.

15. The device of claim 1 comprising a wand-less scanning probe.

16. A method of performing a dental scan, said method comprising the steps of
   a. providing a scanning device of claim 1 and
   b. performing a scanning procedure on a subject or patient.

17. The method of claim 16, said method further comprising the step of
   c. printing, milling, or 3D-printing a dental structure using the information obtained from the scanning procedure.

18. A system for carrying out a dental scan on a patient, said system comprising a portable scanning device of claim 1, and an external device selected form a printer, a milling machine, and a 3D printer.

19. The system of claim 18 further comprising a connecting cable for connecting said device to an external printing, milling, or 3D printing device.

20. The system of claim 18 further comprising a scanning device housing body, a separate mouthpiece, an optional cable for connecting the device to an external printing, milling or 3D printing device, and a carrying case for containing said device, mouthpiece and optional cable.

* * * * *